(12) United States Patent
Yavitz et al.

(10) Patent No.: US 6,312,450 B1
(45) Date of Patent: Nov. 6, 2001

(54) SYSTEM AND METHOD FOR IMPROVING THE APPEARANCE OF SKIN

(75) Inventors: Edward Q. Yavitz, Rockford, IL (US); Michael J. Berry, Pacific Grove, CA (US)

(73) Assignee: Natural Vision Center, Inc., Rockford, IL (US)

( * ) Notice: Subject to any disclaimer, the term of this patent is extended or adjusted under 35 U.S.C. 154(b) by 0 days.

(21) Appl. No.: 09/379,183

(22) Filed: Aug. 23, 1999

Related U.S. Application Data

(63) Continuation-in-part of application No. 08/858,967, filed on May 20, 1997, now Pat. No. 6,009,876.

(51) Int. Cl.[7] .................. A61N 5/06; A61N 5/067
(52) U.S. Cl. .................. 607/88; 607/89; 607/95; 424/400; 424/401; 606/9
(58) Field of Search .................. 606/2, 3, 9–19; 424/59, 400, 401, 484; 607/88, 89, 90, 95

(56) References Cited

U.S. PATENT DOCUMENTS

| | | |
|---|---|---|
| 3,074,407 | 1/1963 | Moon et al. . |
| 4,156,124 | 5/1979 | Macken et al. . |
| 4,406,285 | 9/1983 | Villasenor et al. . |
| 4,461,294 | 7/1984 | Baron . |
| 4,608,392 | 8/1986 | Jacquet et al. . |
| 4,826,828 | 5/1989 | Wilmott et al. . |
| 4,840,175 | 6/1989 | Peyman . |
| 4,903,695 | 2/1990 | Warner et al. . |
| 4,905,711 | 3/1990 | Bennett et al. . |
| 4,976,709 | 12/1990 | Sand . |
| 5,092,863 | 3/1992 | Schanzlin . |
| 5,108,412 | 4/1992 | Krumeich et al. . |
| 5,137,530 | 8/1992 | Sand . |
| 5,186,857 | * 2/1993 | Ramirez et al. ............ 252/167 |
| 5,234,957 | 8/1993 | Mantelle . |
| 5,312,395 | 5/1994 | Tan et al. . |
| 5,336,215 | 8/1994 | Hsueh et al. . |
| 5,356,409 | 10/1994 | Nizzola . |
| 5,437,657 | 8/1995 | Epstein . |
| 5,476,661 | * 12/1995 | Pillai et al. ............ 424/401 |
| 5,582,608 | 12/1996 | Brown . |
| 5,616,139 | 4/1997 | Okamoto . |
| 5,649,922 | 7/1997 | Yavitz . |
| 5,670,547 | 9/1997 | Milstein et al. . |
| 5,846,514 | 12/1998 | Foster et al. . |
| 5,885,596 | 3/1999 | Parab . |
| 5,968,034 | * 10/1999 | Fullmer et al. ............ 606/9 |

FOREIGN PATENT DOCUMENTS

| | | |
|---|---|---|
| 0 531 756 A2 | 3/1993 | (EP) . |
| WO 92/01430 | 2/1992 | (WO) . |
| WO 92/10152 | 2/1992 | (WO) . |
| WO 94/18920 | 9/1994 | (WO) . |
| WO 95/15134 | 6/1995 | (WO) . |

* cited by examiner

*Primary Examiner*—Roy Gibson
(74) *Attorney, Agent, or Firm*—Fletcher, Yoder & Van Someren

(57) ABSTRACT

A cosmetic system and technique are provided for improving the texture and appearance of an individual's skin. The system includes a light transport modifier that may be applied to a portion of the individual's epidermis. The light transport modifier is designed to displace naturally occurring water within that portion. Energy from an appropriate laser, infrared lamp, or the sun can then be directed to a treatment area beneath the epidermal layer without detrimental heat buildup in that area of the epidermis.

50 Claims, 2 Drawing Sheets

SYSTEM AND METHOD FOR IMPROVING THE APPEARANCE OF SKIN

CROSS-REFERENCE TO RELATED APPLICATIONS

This document is a continuation-in-part of patent application, Serial No. 08/858,967, filed May 20, 1997 now U.S. Pat. No. 6,009,876, and entitled System and Method For Modifying and Reshaping Collagen Beneath the Surface of Skin.

FIELD OF THE INVENTION

The present invention relates generally to a cosmetic substance and a method for improving the appearance of skin, and particularly to a topical application that permits energy from the sun to stimulate the release of collagen beneath the epidermis of an individual without damaging the epidermis.

BACKGROUND OF THE INVENTION

Heat has long been used to modify and reshape collagen beneath the surface of the skin. Egyptians used salt, oil and alabaster to improve skin texture and Turks used fire to singe the surface of the skin. In the twentieth century, chemical peels implementing phenol and trichloacetic acid were introduced to reduce wrinkles and remove other anomalies of the skin. Lasers, such as carbon dioxide lasers, were also developed and used for the reduction or elimination of wrinkles, such as periorbital wrinkles, and other anomalies of the skin.

Such methods were more or less effective in reducing or eliminating wrinkles by providing energy in the form of heat to the subepidermal layer, the so-called papillary dermis, between the epidermis and the reticular dermis of an individuals skin. Heat stimulates release of factors that promote new collagen growth and a thicker healthier matrix of elastins and collagen to provide a younger looking skin. However, these techniques result in removal, destruction or damage to the epidermis proximate the area in which heat is applied to the subepidermal layer. The damage or destruction of the epidermis results in redness, loss of body fluid and a greater potential for infection.

For example, with lasers, laser light energy is used to heat tissue beneath the epidermis, but the laser light energy must pass through the epidermis on its way to the treatment area. This laser light energy is absorbed by the epidermis as it passes therethrough and generates unwanted heat that effectively damages or ablates the epidermal layer in the area of treatment. After time, the epidermis heals and grows back over the treatment area.

Attempts have been made to minimize injury to the epidermis by removing heat from the epidermal area proximate the area of treatment. This is typically accomplished by delivering a coolant to the epidermis at the area where it is penetrated by the laser beam. However, this adds to the complexity of the equipment and the procedure.

It would be advantageous to have a light transport modifier that could be applied to the epidermis to permit the transfer of certain types of electromagnetic energy through the epidermis to the area of treatment without absorption of energy and the resultant detrimental buildup of heat in that area of the epidermis.

SUMMARY OF THE INVENTION

The present invention features a topical skin composition. The composition comprises a cosmetic or cosmeceutical material and a light transport modifier mixed with the cosmetic or cosmeceutical material. The light transport modifier is in liquid form and readily absorbed by an epidermal layer of an individual's skin. The light transport modifier permits the passage of infrared energy through the epidermal layer with reduced absorption of energy by that layer.

According to another aspect of the invention, a composition is provided for application to the epidermis of an individual. The composition reduces absorption of certain types of electromagnetic energy that strike the epidermis. The composition comprises a light transport modifier that may be applied to a portion of the epidermis of an individual. The light transport modifier is formulated to displace naturally occurring water within the portion of the epidermis.

According to another aspect of the invention, a method is provide for utilizing energy produced by the sun. The energy is used to improve the appearance of the skin of an individual. The method includes selecting a substance that permits the passage of a desired radiation produced by the sun. The method further includes substantially displacing water that naturally occurs in an epidermal region of an individual with the substance. Thus, when the epidermal region is exposed to the sun, energy from the sun passes through the epidermis and stimulates subepidermal release of collagen.

BRIEF DESCRIPTION OF THE DRAWINGS

The invention will hereafter be described with reference to the accompanying drawings, wherein like reference numerals denote like elements, and.

DETAILED DESCRIPTION OF THE PREFERRED EMBODIMENTS

The present invention includes a system and method by which the outermost layer of a body can be protected while internal tissues are altered, typically by heating. The following discussion will focus on protection of the epidermis during treatment of underlying tissue, but this system and method can also be used on other external layers of the body, such as the epithelium of the eye.

Figure 1:
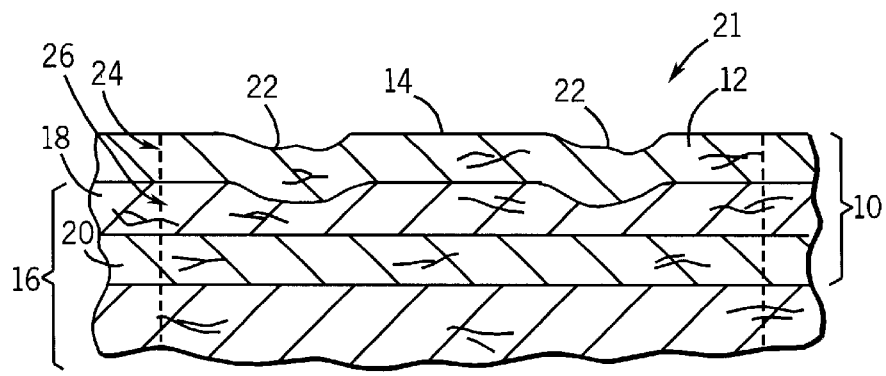
FIG. 1 is a cross-sectional view of a portion of an individual's skin.

Referring generally to FIG. 1, a cross-section of a portion of human skin 10 is illustrated. The skin includes an outer epidermal layer or epidermis 12 having an outer surface 14. Outer surface 14 is the visible surface of an individual's skin.

Additional tissue 16 is disposed beneath epidermis 12 and includes layers of skin 10 as well as deeper tissue. For example, skin 10 includes a papillary dermis layer 18 disposed between epidermis 12 and a reticular dermis layer 20.

In FIG. 1, skin 10 is illustrated as having an anomaly 21, such as wrinkles 22, disposed along a portion 24 of epidermis 12. One way of improving the appearance of skin 10, and particularly portion 24 of epidermis 12, is to heat an area of tissue 16 disposed beneath portion 24. In particular, it is desirable to sufficiently heat a desired treatment area 26 of papillary dermis layer 18. Heating treatment area 26 tends to shrink wrinkles 22 and to stimulate the release of factors that promote new collagen growth and a thicker healthier matrix of elastins and collagen that provide skin 10 with a younger, healthier appearance. This wrinkle reduction effect is also achieved with conventional laser treatment techniques.

Figure 2:
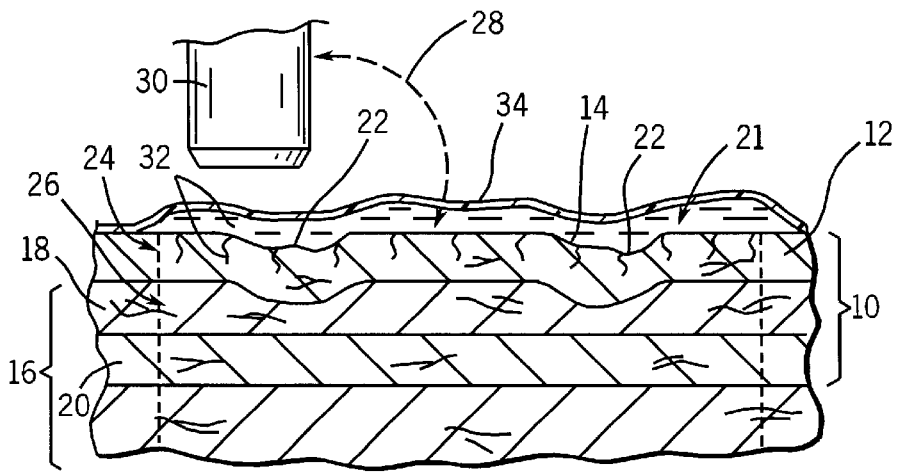
FIG. 2 is a cross-sectional view similar to FIG. 1 but with a light transport modifier applied.

Referring now to FIG. 2, a system 28 according to a preferred embodiment of the present invention, is illustrated. System 28 includes an energy emitter 30, a light transport modifier 32 and a protectant layer 34 disposed over light transport modifier 32 after it is applied to portion 24 of epidermis 12.

Energy emitter 30 preferably emits energy in the form of electromagnetic radiation that can be absorbed by tissue 16, e.g., desired treatment area 26 of layer 18, to create heat within that tissue area. Said energy emitter would preferably have an energy absorption coefficient in the range of 50 to 500 $cm^{-1}$ which inversely corresponds to a treatment penetration of 20 to 200 $\mu m$ depth, in the absence of significant light scattering. Light transport modifier 32 preferably acts as light absorption and light scattering modifier that permits heat energy to be absorbed by papillary dermis layer 18 while limiting heat absorption in epidermis 12.

It should be understood that a goal of the present invention is to optimize light treatment and subsequent heating of the papillary dermis while preventing significant damage to the epidermis. Both absorption and scattering of light can be modified by the use of light transport modifiers described herein. The effective optical absorption coefficient $\mu_{eff}$ includes both absorption and scattering coefficients, as discussed in Optical-Thermal Response of Laser-Irradiated Tissue (Jacques SL, Wang L. Monte Carlo modeling of energy absorption in tissues. In: Welch AJ, van Gemert MJC (editors). *Optical-Thermal Response of Laser-Irradiated Tissue*. (Plenum Press, New York, 1995), pp. 73–100). A preferred embodiment of this invention reduces $\mu_{eff}$ for the epidermal layer while retaining a large value of $\mu_{eff}$ for the papillary dermal layer. The effects of thermal conduction are not significant for short duration pulses of light (e.g., 1 ms or shorter) that will typically be used with man-made light sources. However, with longterm irradiation by light sources such as the sun, thermal conduction will tend to equilibrate the temperature distributions of the papillary dermal layer with those in the epidermal layer. In this case, it may be desirable to include a cooling window, e.g. a heat sink or other cooling means in contact with the epidermal layer in order to maintain a significant temperature gradient and prevent damage to the epidermis. An even better approach toward protecting the epidermis is to use a combined index-matching and cooling fluid in contact with the epidermis. Index-matching (of a fluid such as a lotion) to the tissue refractive index of ca. 1.3 increases the remittance of light from the epidermis (so that less light is ultimately absorbed by the epidermis, leading to less heating of this layer). Convective cooling of this fluid/lotion by air circulation provided by, for example, a fan would further cool the epidermis and maintain a protective temperature gradient.

Effective optical absorption is a function of the initial light source distribution (in terms of the photon wavelength distribution and the photon energy, polarization, and angle-of-incidence distributions over the surface of the tissue), the tissue optical properties (i.e., the absorption coefficient, the scattering coefficient, and the scattering anisotropy factor, all of which are photon wavelength dependent), the temporal history of light/tissue interactions (which may modify the tissue optical properties during, and after, the light treatment), and other parameters. Examples of the effective absorption of light in tissue as a function of some of these parameters are presented and discussed in the Optical-Thermal Response of Laser-Irradiated Tissue article referenced above. Importantly, in short wavelength spectral regions (ca. 0.7 to 2 $\mu m$), scattering coefficients of skin are typically much larger than absorption coefficients at most wavelengths, so the energy absorption is dominated by scattering which tends to increase the optical absorption of the skin near the front surface onto which light is initially delivered, compared to the case in which little or no scattering occurs. Thus, the effective optical absorption (and, consequently, the optical heating) of a highly scattering tissue near its front surface can be much larger than the optical absorption of a non-scattering tissue."

When the light scattering coefficient is large compared to the absorption coefficient at shorter wavelengths; that is, below ca. 2 $\mu m$ light wavelength, the energy emitter could produce the desired treatment effects using light for which the absorption coefficient is even below 1 $cm^{-1}$, thus permitting the use of an energy emitter having an energy absorption coefficient in the range of 50 $cm^{-1}$ to 1 $cm^{-1}$ and even below 1 $cm^{-1}$. In the preferred embodiment, energy emitter 30 is a light emitter, such as a 5 to 6 $\mu m$ emitting carbon monoxide laser or a Tm:YAG laser having a wavelength of approximately 2 $\mu m$. Energy emitter 30 also can be a non-laser light emitter, such as an infrared light emitter and specifically a pulsed infrared lamp or a disposable chemical light source. The papillary dermal layer in a person's skin could be treated by this system with sunlight energy at the lowest absorption coefficients due to the high scattering coefficient in skin for visible light having that wavelength.

If a laser light energy emitter is used, it can be mounted on a mechanical stage or hand-held by a person providing the skin rejuvenation treatment. In either case, the energy emitter 30 is oriented to direct energy through portion 24 of epidermis 12 to the desired treatment area, such as area 26. The energy emitter 30 is moved along outer surface 14 of portion 24 until the area of anomaly 21 has been fully treated such that over time, the anomaly, e.g. wrinkles 22, has been reduced or eliminated. Handling and movement of the laser is comparable to the procedures currently employed by those conducting conventional laser treatments.

Potentially, the laser light can be diffused over a greater area, or a large infrared lamp can be used to direct energy toward a relatively large portion of epidermis 12 for absorption by a relatively large desired treatment area 26. In fact, the energy may be provided by multiple infrared lamps distributed through, for example, a tanning bed to promote widespread reinvigoration of skin. Of course, the time of exposure to energy from energy emitter 30 will vary depending on the power of the energy and the area over which it is spread.

Light transport modifier 32 is a material formulated to cooperate with epidermis 12 to permit light energy, such as laser light from a carbon monoxide or Tm:YAG laser or light from an infrared lamp, to pass through portion 24 of epidermis 12 with reduced or no absorption of the energy by the tissue of epidermis 12. This permits treatment of tissue beneath the epidermis via appropriate lasers or infrared emitters (see FIG. 3) without detrimental heat buildup in portion 24 of epidermis 12. Thus, there is no damage or ablation of portion 24. Additionally, because energy absorption by epidermis 12 is reduced or eliminated, it is not necessary to continuously remove heat from portion 24 via a coolant. This improves the safety and effectiveness of skin rejuvenation with the aid of lasers or other energy emitters designed to stimulate tissue beneath the epidermal layer.

Preferably, light transport modifier 32 is formulated to displace the naturally occurring water ($^1H_2^{16}O$) within portion 24 when applied to epidermis 12. This water within the epidermal layer absorbs energy from certain lasers or other energy emitters, such as those described above, and results in the damaging heat buildup within epidermis 12. By displacing some or all of the water within portion 24 of epidermis 12, the energy from these types of energy emitters is permitted to pass through the epidermal layer to the subepidermal layer 18 or other tissue beneath epidermis 12. The result is reduced heat buildup in portion 24 of epidermis 12 during the treatment procedure. The epidermis remains intact which lessens the chance of infection, decreases redness and loss of body fluid and substantially shortens the healing time.

Figure 3:
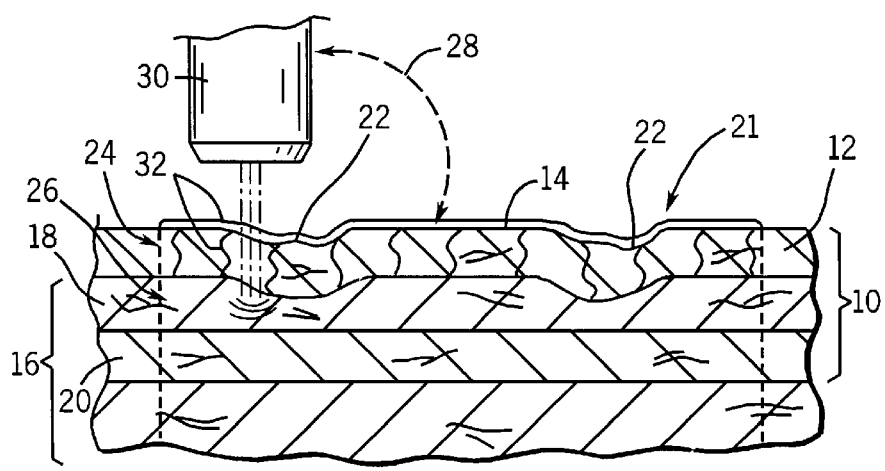
FIG. 3 is a cross-sectional view similar to that of FIG. 2 but also showing a light emitter interacting with the tissue beneath the epidermis.

Light transport modifier 32 is typically in liquid form and preferably comprises deuterated water (an equilibrium mixture of $D_2O$, HDO, and $H_2O$). Deuterated water is understood to be a mixture of the three species listed in which deuterium is present at significantly larger amounts than its natural abundance (ca. 0.015%). Deuterium oxide includes dideuterium oxide, $D_2O$, and monodeuterium monohydrogen oxide, HDO, which are isotopic variants of the predominant naturally occurring water ($^1H_2^{16}O$). Dideuterium oxide is an isotope of water that can be represented as $^2H_2 16O$. Monodeuterium monohydrogen oxide is an isotope of water that can be referenced as $^1H_2HO$ or HDO. However, other isotopic variants of the predominant naturally occurring water potentially can be utilized, such as $^1H_2{}^{18}O$, $^2H_2{}^{18}O$, $^{17}O$ variants, partly deuterated water and other isotopic variants. These chemicals/isotopes are able to replace the primary natural water content of the epidermis or the epithelium of the eye to permit energy to pass through to tissues beneath this outer layer, as best illustrated in FIG. 3.

After light transport modifier 32 is applied to portion 24 of epidermis 12, it typically is covered by protectant layer 34. With certain chemicals, such as deuterium oxide, evaporation can occur relatively rapidly and protectant layer 34 helps prevent this occurrence as light transport modifier 32 is absorbed by epidermis 12 to displace the natural water content in portion 24. Typically, protectant layer 34 is impermeable or semi-permeable to air. For example, protectant layer 34 can be an occlusive dressing consisting of a sheet of plastic applied over light transport modifier 32 and epidermis 12. Potentially, energy can be directed through protectant layer 34 towards the desired treatment area 26, but it is preferred that protectant layer 34 be removed prior to stimulating the desired treatment area 26 via energy emitter 30.

In practicing the invention, dead skin cells typically are exfoliated from epidermis 12 along outer surface 14 of portion 24. Dilute glycolic acid or other alpha-hydroxy acids can be used to exfoliate the dead skin. Following exfoliation, light transport modifier 32 is applied to portion 24 and covered by protectant layer 34. Light transport modifier 32 is provided sufficient time to be absorbed by portion 24, thereby displacing the water normally within that part of the epidermal layer. The protectant layer 34 is then removed and energy emitter 30 is used to direct energy through portion 24 to desired treatment area 26 . As with conventional techniques, the energy supplied to desired treatment area 26 must sufficiently heat the area to shrink wrinkles and stimulate the release of factors that promote new collagen growth.

After treatment of area 26, the epidermis 12 remains intact and the individual is left with healthier, younger looking skin. Continuous biosynthesis of new collagen with subsequent remodeling will occur over several months after treatment.

Figure 4:
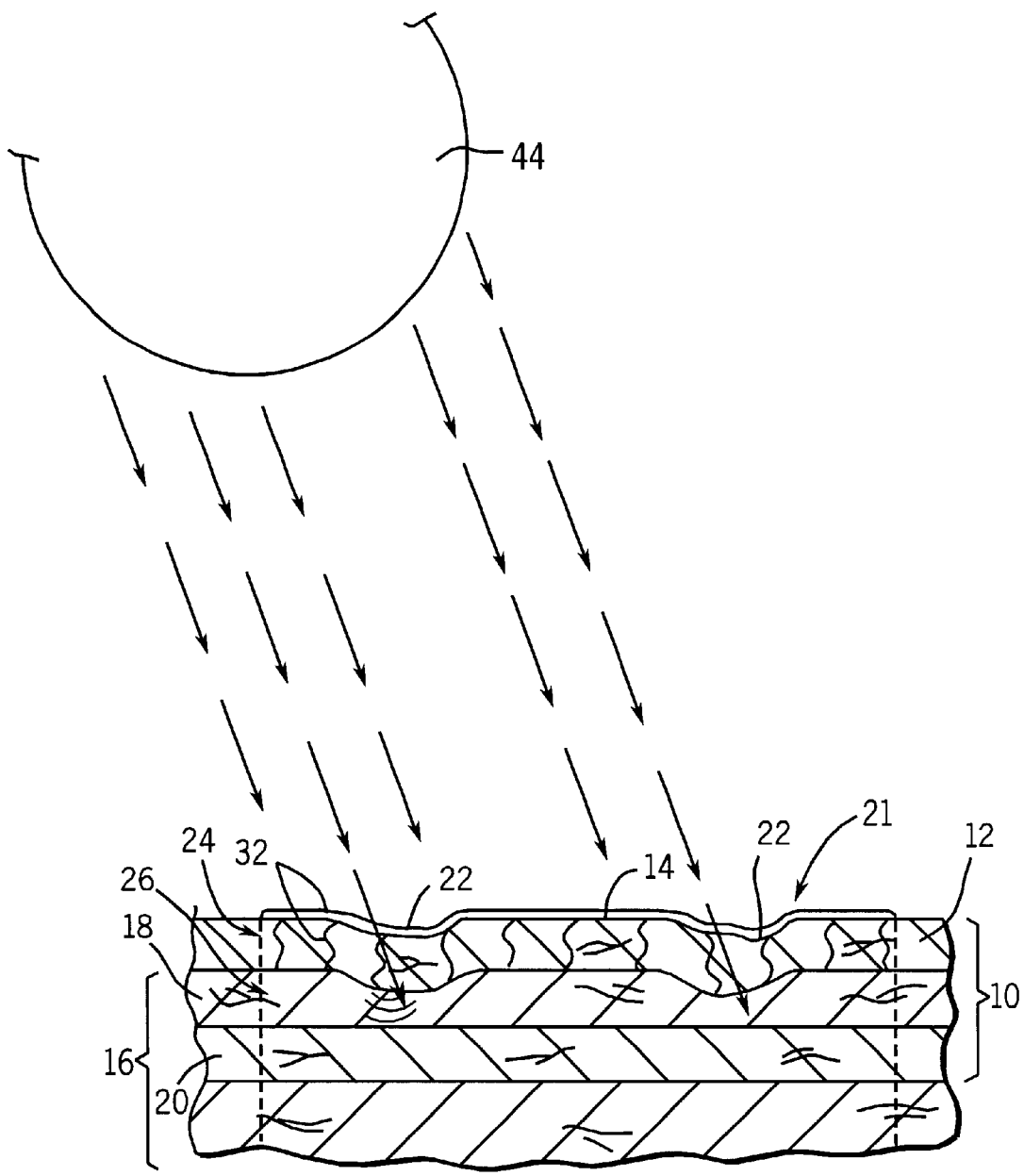
FIG. 4 is a cross-sectional view similar to that of FIG. 3 showing a light transport modifier mixed with a cosmetic or cosmeceutical material applied to the skin of an individual to permit passage of energy from the sun through the epidermal layer.

In another embodiment of the present invention, energy from the sun can be used to provide heat to a subepidermal layer for the stimulation of collagen release and the reduction of anomalies in the skin. As illustrated in FIG. 4, light transport modifier 32 may be mixed with a cosmetic or cosmeceutical material 40 that is applied to the epidermis 12. Cosmetic and cosmeceutical materials 40 may constitute skin care and cosmetic creams, lotions, skin cleansers, moisturizers, ultraviolet blocking agents, perfumes, makeup, foundation, lipsticks, eyeshadow, deodorants, and topical medicinal substances such as tretinoin, alpha-hydroxy acids, herbs, botanicals, animal extracts and vitamin E, vitamin C. Cosmetic or cosmeceutical material 40 may constitute a medicinal substance or a cream or lotion. For example, the naturally occurring water within sunscreen can be replace with an isotopic variant, such as deuterated water. When this lotion is applied to epidermis 12, the light transport modifier 32, e.g. deuterated water, diffuses into epidermis 12 and facilitates the passage of energy 42, such as infrared energy from the sun 44, as illustrated in FIG. 4.

Preferably, the cosmetic or cosmeceutical material 40 includes cosmetic compositions, such as those in the form of liquid emulsions (lotions) or thicker emulsions (creams), but the cosmetic or cosmeceutical material can be in the form of lotions, creams, solutions, suspensions, anhydrous salves, sticks, gels, emulsions, ointments, plasters, patches, films, tapes or dressing preparations, all of which are known to those of ordinary skill in the art of topical skin formulations and preparations. In each of these examples, the water normally utilized in the mixture is replaced with a light transport modifier 32, such as deuterated water.

Two specific examples of a cosmetic or cosmeceutical material mixed with a light transport modifier, such as deuterated water, are presented in the following tables A and B:

TABLE A

| Ingredient | % w/w |
|---|---|
| Propylene glycol | 5.0 |
| Stearyl alcohol | 4.0 |
| Dibutyl adipate | 3.0 |
| Isopropyl myristate | 3.0 |
| Steareth-2 | 2.5 |
| Steareth-21 | 2.5 |
| Magnesium aluminum silicate | 2.0 |
| Dimethicone | 1.0 |
| Laureth-4 | 1.0 |
| Cetyl alcohol | 0.5 |
| Glyceryl monostearate SE | 0.5 |
| Sorbic acid | 0.2 |
| Deuterated water | 74.8 |

TABLE B

| Ingredient | % w/w |
|---|---|
| Mineral Oil | 7.0 |
| Stearyl alcohol | 4.0 |
| Glycerin | 3.0 |
| Steareth-2 | 2.5 |
| Steareth-21 | 2.5 |
| Dibutyl adipate | 1.0 |

TABLE B-continued

| Ingredient | % w/w |
|---|---|
| Isopropyl myristate | 1.0 |
| Dimethicone | 1.0 |
| Laureth-4 | 1.0 |
| Propylene glycol | 1.0 |
| Cetyl alcohol | 0.5 |
| Glyceryl monostearate SE | 0.5 |
| Sorbic acid | 0.2 |
| Deuterated water | 74.8 |

It should be understood to those skilled in the art that mixtures such as those illustrated in Tables A and B will tend to equilibrate in their isotopic compositions. For example, when organic compounds such as propylene glycol and stearyl alcohol are dissolved in deuterated water (which itself may be an equilibrium mixture of $D_2O$, HDO, and $H_2O$), some of the hydrogen atoms of the organic compounds may exchange with the deuterium atoms of the deuterated water, leading to an isotopic mixture that contains partly-deuterated organic compounds. Labile hydrogen atoms such as those associated with hydroxyl groups (contained in all alcohols, diols, and other organic compounds) exchange very rapidly with deuterium atoms in deuterated water while less labile hydrogen atoms such as those associated with methyl groups exchange slowly. Therefore, the actual isotopic composition of a topical skin formulation may depend on initial composition, storage time, temperature, solution pH (for acid-catalyzed and/or base-catalyzed exchange reactions), and other variables. It should be understood that the exact formulation used will be designed to optimize skin treatment and rejuvenation while maintaining a protective effect for the epidermis. It should also be understood that the formulation will be customized for different skin types (e.g., more UV blocker for unpigmented skin) and for different amounts of skin photodamage, including skin wrinkling. Dose requirements (for both the amount of the formulation applied to a skin area and the amount of light treatment) may also be customized for different skin types, photodamage, age, and other factors.

It should further be understood that the isotopic composition of skin (as well as its optical properties of absorption, scattering, etc.) will depend upon the amount of topical skin formulation applied, the time after application, and other variables. In general, light transport modifiers will be transported from the outer surface of the epidermis through the epidermis and into the papillary dermis with rates that depend upon the transport mechanism of each modifier, the time after application, and other factors. There will therefore be a depth profile of each material applied to the epidermis that is a function of time, concentration of material, isotopic exchange reaction of the material with initial skin constituents such as ordinary water, etc.

When applications, such as those listed above in Tables A and B, are applied to epidermis 12, energy 42, and particularly infrared energy, from sun 44 substantially passes through epidermis 12 for absorption in subepidermal layer 18. As described above, the heating of the subepidermal area 26 tends to shrink wrinkles 22 by stimulating the release of factors that promote new collagen growth and a thicker healthier matrix of elastins and collagen, providing skin 10 with a younger, healthier appearance.

An exemplary list of lotions, creams and other compositions that potentially can be used as a cosmetic or cosmeceutical material in the present invention is listed in U.S. Pat. No. 4,608,392, issued Aug. 26, 1986, columns 6 through 13. In these compositions, the normal water is replaced with an appropriate isotopic variant, such as deuterated water. In these and other formulations, the light transport modifier mixed into the composition displaces the naturally occurring water in the epidermal layer when the composition is applied to an individual's skin. As the light transport modifier is absorbed into the epidermis, there is a greater passage of infrared energy to the subepidermal layer or layers.

A further benefit of isotopically modifying one or more of the ingredients contained in topical skin care cosmeceutical and cosmetic topical products is that when stable isotopes are incorporated in some of these ingredients, they tend to last longer and become more effective. The use of isotopic variants to replace one or more of the most naturally abundant isotopic elemental atoms found in cosmetic and cosmeceutical ingredients such as skin cleansers, moisturizers, ultraviolet blocking agents, perfumes, makeup, foundation, lipsticks, eyeshadow, deodorants, and topical medicinal substances such as tretinoin, alpha-hydroxy acids, herbs, botanicals and vitamin E, vitamin C and, of course, naturally occurring water $^1H_2^{16}O$), will change their absorption spectra as well as enhancing the pharmacokinetics of these isotopically modified ingredients, thus improving their duration and effectiveness in human skin. Specifically, these cosmetic and cosmeceutical ingredients would be isotopically modified by replacing one or more of their common chemical elements, such as H, $^{16}O$, $^{12}C$, $^{14}N$ with their stable but less abundant isotopic variants Deuterium, $^{17}O$ or $^{18}O$, $^{13}C$, $^{15}N$, respectively. Other biologically significant chemical elements such as calcium, sulfur, iron, boron, potassium, chlorine, zinc, lithium, and magnesium which are commonly present in cosmetic and cosmeceutical preparations could also be isotopically modified in order to alter the energy absorption characteristics and improve the pharmacokinetic duration and effectiveness of the ingredients containing them.

An exemplary list of chemical elements having stable but less abundant isotopic variants is presented in the following Table C. The less abundant isotopes can be substituted for their more common counterparts in cosmetic and cosmeceutical preparations to alter the energy absorption characteristics and improve the pharmacokinetic duration and effectiveness of the ingredients containing them.

TABLE C

| Element | Isotope | Natural Abundance (%) |
|---|---|---|
| Hydrogen | $^1H$ | 99.985 |
| | $^2H$ | 0.015 (Deuterium (D)) |
| Lithium | $^6Li$ | 7.5 |
| | $^7Li$ | 92.5 |
| Boron | $^{10}B$ | 20 |
| | $^{11}B$ | 80 |
| Carbon | $^{12}C$ | 98.89 |
| | $^{13}C$ | 1.11 |
| Nitrogen | $^{14}N$ | 99.64 |
| | $^{15}N$ | 0.36 |
| Oxygen | $^{16}O$ | 99.76 |
| | $^{17}O$ | 0.04 |
| | $^{18}O$ | 0.20 |
| Magnesium | $^{24}Mg$ | 78.99 |
| | $^{25}Mg$ | 10.00 |
| | $^{26}Mg$ | 11.01 |
| Sulfur | $^{32}S$ | 95.0 |
| | $^{33}S$ | 0.76 |
| | $^{34}S$ | 4.22 |
| Chlorine | $^{35}Cl$ | 75.77 |
| | $^{37}Cl$ | 24.23 |

TABLE C-continued

| Element | Isotope | Natural Abundance (%) |
|---|---|---|
| Potassium | $^{39}$K | 93.26 |
| | $^{40}$K | 0.01 |
| | $^{41}$K | 6.73 |
| Calcium | $^{40}$Ca | 96.941 |
| | $^{42}$Ca | 0.647 |
| | $^{43}$Ca | 0.135 |
| | $^{44}$Ca | 2.086 |
| | $^{46}$Ca | 0.004 |
| | $^{48}$Ca | 0.187 |
| Iron | $^{54}$Fe | 5.8 |
| | $^{56}$Fe | 91.8 |
| | $^{57}$Fe | 2.1 |
| | $^{58}$Fe | 0.3 |
| Zinc | $^{64}$Zn | 48.6 |
| | $^{66}$Zn | 27.9 |
| | $^{67}$Zn | 4.1 |
| | $^{68}$Zn | 18.8 |
| | $^{70}$Zn | 0.6 |

The most important stable isotopic modifications are those for hydrogen, carbon, nitrogen, and oxygen. Each of these elements has one principal most abundant isotope, so enrichment by modification to one or more of the rarer isotopes makes a large change in composition. Also, differences in absorption spectra and pharmacokinetics for various isotopes of a given element are, in general, larger for these light elements (especially for deuterium compared to hydrogen). As the atomic masses of the elements and their isotopes increase, differences between their isotopic variants decrease.

It will be understood that the foregoing description is of preferred embodiments of this invention, and that the invention is not limited to the specific forms shown. For example, a variety of energy emitters may be used, the intensity of the energy and time over which it is directed against the skin of an individual will vary depending on the degree and type of the anomalies, e.g., wrinkles, being treated. Although this system and method may most readily be used to reduce or eliminate wrinkles in various locations of an individual's face, the system and method can be used to modify and reshape collagen beneath the outer surface of the body in other areas, including an individual's eyes. Additionally, the light transport modifier can be formulated in several different ways. These and other modifications may be made in the design and arrangement of the elements without departing from the scope of the invention as expressed in the appended claims.

What is claimed is:

1. An isotopically modified topical skin composition, comprising:
    a cosmetic or cosmeceutical material; and
    a light transport modifier mixed with the cosmetic or cosmeceutical material, wherein the light transport modifier is in liquid form and readily absorbed by an epidermal layer of mammalian skin to permit passage of infrared energy through the epidermal layer with reduced absorption of said energy by the epidermal layer.

2. The isotopically modified topical skin composition as recited in claim 1, wherein the light transport modifier causes at least partial isotopic modification of the cosmetic or cosmeceutical material, including replacement of at least a portion of a common elemental atom contained in the cosmetic or cosmeceutical material with a stable, less common, isotopic variant.

3. The isotopically modified topical skin composition as recited in claim 2, wherein common elemental atom is H and the stable isotopic variant is deuterium.

4. The isotopically modified topical skin composition as recited in claim 2, wherein common elemental atom is $^{16}$O and the stable isotopic variant is $^{17}$O.

5. The isotopically modified topical skin composition as recited in claim 2, wherein common elemental atom is $^{16}$O and the stable isotopic variant is $^{18}$O.

6. The isotopically modified topical skin composition as recited in claim 2, wherein common elemental atom is $^{12}$C and the stable isotopic variant is $^{13}$C.

7. The isotopically modified topical skin composition as recited in claim 2, wherein common elemental atom is $^{14}$N and the stable isotopic variant is $^{15}$N.

8. The isotopically modified topical skin composition as recited in claim 1, wherein the light transport modifier promotes isotopic modification of the cosmetic or cosmeceutical material, including replacement of at least a portion of a biologically significant chemical element present in the composition and selected from the group consisting of boron, sulfur, iron, lithium, potassium, chlorine, zinc, calcium, magnesium, and their isotopic variants.

9. The isotopically modified topical skin composition as recited in claim 1, wherein the light transport modifier is formulated to displace naturally occurring water in the epidermal layer.

10. The isotopically modified topical skin composition as recited in claim 9, wherein the light transport modifier comprises an isotopic variant of naturally occurring water.

11. The isotopically modified topical skin composition as recited in claim 10, wherein the isotopic variant comprises deuterated water.

12. The isotopically modified topical skin composition as recited in claim 10, wherein the isotopic variant comprises $H_2{}^{18}O$.

13. The isotopically modified topical skin composition as recited in claim 10, wherein the isotopic variant comprises $H_2{}^{17}O$.

14. The isotopically modified topical skin composition as recited in claim 1, wherein the cosmetic or cosmeceutical material comprises a therapeutic substance.

15. The isotopically modified topical skin composition as recited in claim 1, wherein the cosmetic or cosmeceutical material comprises a perfume.

16. The isotopically modified topical skin composition as recited in claim 1, wherein the cosmetic or cosmeceutical material comprises a deodorant.

17. The isotopically modified topical skin composition as recited in claim 1, wherein the cosmetic or cosmeceutical material comprises a skin care product selected from the group consisting of cleansers, tretinoin, alpha-hydroxy acids, herbs, botanicals, animal extracts, vitamin E and vitamin C.

18. A composition for application to an epidermis of an individual to reduce absorption of certain types of electromagnetic energy that strike the epidermis, comprising:
    a light transport modifier that may be applied to a portion of the epidermis of an individual, the light transport modifier being formulated to reduce absorption of certain types of electromagnetic energy and to displace naturally occurring water within the portion of the epidermis.

19. The composition as recited in claim 18, further comprising an exfoliant.

20. The composition as recited in claim 18, wherein the light transport modifier comprises deuterated water.

21. The composition as recited in claim 18, wherein the light transport modifier is formulated to reduce the absorption of electromagnetic energy having wavelengths within the infrared region of the electromagnetic radiation spectrum.

22. The composition as recited in claim 18, further comprising a lotion.

23. The composition as recited in claim 18, further comprising a cream.

24. The composition as recited in claim 18, further comprising a perfume.

25. The composition as recited in claim 18, further comprising a skin care therapeutic substance.

26. The skin care therapeutic substance as recited in claim 25, further comprising a substance selected from the group consisting of moisturizers, cleansers, tretinoin, alpha-hydroxy acids, herbs, botanicals, animal extracts, vitamin E and vitamin C.

27. A method for utilizing infrared energy to improve the appearance of skin of an individual, comprising:

selecting an isotopically modified substance that permits passage of a desired radiation in the infrared region through the epidermis;

applying the isotopically modified substance to an area of the epidermis; and heating the papillary dermis layer between the epidermis and the reticular dermis at the area in order to stimulate the release of factors that promote new collagen growth.

28. The method as recited in claim 27, wherein heating comprises utilizing the infrared energy found in naturally occurring sunlight.

29. The method as recited in claim 27, wherein heating comprises utilizing infrared energy emitted from a man-made energy source creating light having an energy absorption coefficient in the range of 50 to 500 $cm^{-1}$ which inversely corresponds to a primary treatment penetration of 20 to 200 $\mu$m depth in the absence of strong light scattering.

30. The method as recited in claim 27, wherein heating comprises utilizing an infrared energy source for which the absorption coefficient is in the range of 1 $cm^{-1}$ to 50 $cm^{-1}$ and for which strong light scattering contributes to radiation transport.

31. The method as recited in claim 28, wherein utilizing includes utilizing a Tm:YAG laser.

32. The method as recited in claim 29, wherein utilizing includes utilizing a pulsed infrared lamp.

33. The method as recited in claim 29, wherein utilizing includes utilizing a disposable chemical light source.

34. The method as recited in claim 30, wherein utilizing includes exposing the area to sunlight.

35. The method as recited in claim 30, further comprising mixing the isotopically modified substance with a cosmetic or cosmeceutical material such that at least a portion of a common chemical element contained in the cosmetic or cosmeceutical material is replaced with a stable isotopic variant.

36. The method as recited in claim 35, wherein the common chemical element is H and the stable isotopic variant is deuterium.

37. The method as recited in claim 35, wherein the common chemical element is $^{16}O$ and the stable isotopic variant is $^{17}O$.

38. The method as recited in claim 35, wherein the common chemical element is $^{16}O$ and the stable isotopic variant is $^{18}O$.

39. The method as recited in claim 35, wherein the common chemical element is $^{12}C$ and the stable isotopic variant is $^{13}C$.

40. The method as recited in claim 35, wherein the common chemical element is $^{14}N$ and the stable isotopic variant is $^{15}N$.

41. The method as recited in claim 27, wherein selecting includes selecting an isotopic variant of naturally occurring water.

42. The method as recited in claim 41, wherein selecting includes selecting deuterated water.

43. The method as recited in claim 41, wherein selecting includes selecting $H_2{}^{18}O$.

44. The method as recited in claim 41, wherein selecting includes selecting $H_2{}^{17}O$.

45. The method as recited in claim 28, further comprising mixing the isotopically modified substance into a lotion as a substitute for the normal $^1H_2{}^{16}O$.

46. The method as recited in claim 27, further =comprising cooling the epidermis at the area.

47. The method as recited in claim 46, wherein cooling comprises conductively cooling the epidermis at the area.

48. The method as recited in claim 46, wherein cooling comprises convectively cooling the epidermis at the area.

49. A method for improving the effectiveness of a cosmetic or cosmeceutical composition, comprising:

providing a cosmetic or cosmeceutical composition; and isotopically modifying at least one of the chemical elements contained in the cosmetic or cosmeceutical composition to alter the energy absorption characteristics and the pharmacokinetic properties of the cosmetic or cosmeceutical composition.

50. The method as recited in claim 49, wherein isotopically modifying comprises modifying a chemical element selected from the group consisting of H, $^{16}O$, $^{12}C$, $^{14}N$, and the most abundant stable isotopes of sulfur, iron, potassium, chlorine, zinc, lithium, boron, calcium and magnesium with their less abundant stable isotopic variants.

* * * * *